(12) United States Patent
Bui et al.

(10) Patent No.: US 9,095,527 B2
(45) Date of Patent: Aug. 4, 2015

(54) COMPOSITIONS CONTAINING ACRYLIC THICKENER

(75) Inventors: Hy Si Bui, Piscataway, NJ (US);
Chunhua Li, Scotch Plains, NJ (US);
Dhaval Patel, Edison, NJ (US);
Mohamed Kanji, Edison, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 13/695,917

(22) PCT Filed: May 5, 2011

(86) PCT No.: PCT/US2011/035369
§ 371 (c)(1),
(2), (4) Date: Dec. 31, 2012

(87) PCT Pub. No.: WO2011/140348
PCT Pub. Date: Nov. 10, 2011

(65) Prior Publication Data
US 2013/0101542 A1    Apr. 25, 2013

Related U.S. Application Data

(60) Provisional application No. 61/331,622, filed on May 5, 2010.

(51) Int. Cl.

| | |
|---|---|
| *A61Q 1/00* | (2006.01) |
| *A61Q 1/10* | (2006.01) |
| *A61K 8/81* | (2006.01) |
| *A61K 8/37* | (2006.01) |
| *A61K 8/891* | (2006.01) |
| *A61K 8/92* | (2006.01) |
| *A61Q 1/02* | (2006.01) |
| *A61Q 1/04* | (2006.01) |
| *A61Q 1/06* | (2006.01) |
| *A61Q 19/00* | (2006.01) |

(52) U.S. Cl.
CPC ............. *A61K 8/8152* (2013.01); *A61K 8/37* (2013.01); *A61K 8/891* (2013.01); *A61K 8/92* (2013.01); *A61K 8/922* (2013.01); *A61Q 1/02* (2013.01); *A61Q 1/04* (2013.01); *A61Q 1/06* (2013.01); *A61Q 1/10* (2013.01); *A61Q 19/001* (2013.01)

(58) Field of Classification Search
CPC .......... A61Q 1/00; A61Q 1/10; A61K 8/8152
USPC ................................. 424/401, 70.7
See application file for complete search history.

(56) References Cited

U.S. PATENT DOCUMENTS

| | | | |
|---|---|---|---|
| 5,534,247 | A | 7/1996 | Franjac et al. |
| 6,214,329 | B1 * | 4/2001 | Brieva et al. ................. 424/70.7 |
| 7,837,984 | B2 | 11/2010 | McNamara et al. |
| 7,837,985 | B2 | 11/2010 | McNamara et al. |
| 7,846,424 | B2 | 12/2010 | McNamara et al. |
| 2005/0249684 | A1 * | 11/2005 | Dobkowski et al. ............ 424/66 |
| 2006/0088486 | A1 | 4/2006 | McNamara et al. |
| 2008/0196174 | A1 * | 8/2008 | Schmenger et al. ............. 8/406 |
| 2009/0035242 | A1 | 2/2009 | Maes et al. |
| 2011/0274636 | A1 | 11/2011 | Perruna et al. |
| 2012/0171141 | A1 | 7/2012 | Bui et al. |
| 2012/0171142 | A1 | 7/2012 | Bui et al. |
| 2012/0171145 | A1 | 7/2012 | Bui et al. |

FOREIGN PATENT DOCUMENTS

DE       19746468 A1 *  4/1999

OTHER PUBLICATIONS

Dow Corning Corporation, "Dow Corning® 5225C Formulation Aid", Nov. 20, 2012, Material Safety Data Sheet, pp. 1-8.*
Seppic, Simulgel EG Emuslifying-Thickening Polymer A Formulator's Essential Partner!, Mar. 2005, pp. 1-39.*
U.S. Appl. No. 13/696,145, filed Nov. 5, 2012, Li, et al.
U.S. Appl. No. 13/696,159, filed Nov. 5, 2012, Wahl, et al.
U.S. Appl. No. 13/844,518, filed May 9, 2013, Kanji, et al.
U.S. Appl. No. 13/844,153, filed May 8, 2013, Li, et al.
U.S. Appl. No. 13/844,122, filed May 8, 2013, Li, et al.
U.S. Appl. No. 13/988,360, filed May 21, 2013, Li, et al.
International Search Report Issued Feb. 8, 2012 in PCT/US11/35369 Filed May 5, 2011.

* cited by examiner

*Primary Examiner* — Ali Soroush
(74) *Attorney, Agent, or Firm* — Oblon, McClelland, Maier & Neustadt, L.L.P.

(57) ABSTRACT

The invention relates to a composition, especially a cosmetic composition, comprising at least one acrylic thickener having a high viscosity and a low solids content, as well as to methods of using such compositions.

33 Claims, 1 Drawing Sheet

COMPOSITIONS CONTAINING ACRYLIC THICKENER

CROSS-REFERENCE TO RELATED APPLICATIONS

This application claims the benefit of priority under 35 U.S.C. §119(e) from U.S. Provisional Application Ser. No. 61/331,622, filed May 5, 2010, the entire contents of which is hereby incorporated by reference.

FIELD OF THE INVENTION

The present invention relates to compositions comprising at least one acrylic thickener. Among other improved or beneficial properties, compositions containing both an acrylic thickener and high viscosity oil have surprisingly good texture, spreadability, pick up and feel properties, as well as good skin adherence properties.

DISCUSSION OF THE BACKGROUND

Many cosmetic compositions, including pigmented cosmetics such as foundations, concealers, lipsticks, and mascaras, and other cosmetic and sunscreen compositions, have been formulated in an attempt to posses good feel and texture upon application. Unfortunately, many of these compositions can be difficult to apply and do not possess a soft texture or smooth feel upon application. Moreover, such compositions oftentimes have a tendency to feel tacky, yielding poor application and spreadability characteristics.

Silicone elastomers have been added to cosmetic compositions to improve the feel of the compositions. However, the use of silicone elastomers can be problematic, given their expense and that they can be difficult to formulate owing to their chemical make up—for example, compositions including silicone elastomers can be unstable, particularly if uncomplimentary compounds are added to an elastomer-containing composition.

Thus, there remains a need for improved cosmetic compositions having improved cosmetic properties, particularly good feel and texture characteristics upon application, without relying solely (if at all) upon silicone elastomers.

Accordingly, one aspect of the present invention is a care and/or makeup and/or treatment composition for lips which has good cosmetic properties such as, for example, good shine, feel and/or texture properties upon application.

SUMMARY OF THE INVENTION

The present invention relates to compositions comprising at least one acrylic thickener and at least one oil.

The present invention also relates to colored compositions comprising at least one coloring agent, at least one acrylic thickener, and at least one oil. Such colored compositions can be, for example, cosmetic compositions such as lip compositions (for example, lipstick or liquid lip colors), mascaras, eyeshadows or foundations.

The present invention further relates to compositions comprising at least one acrylic thickener, at least one oil, and water. Preferably, such compositions contain a majority of water (that is, at least 50%) and are in the form of an emulsion. Such water-containing compositions preferably further contain at least one coloring agent and are preferably foundations, lip compositions, nail polishes or mascaras.

The present invention also relates to methods of treating, caring for and/or making up keratinous material (for example, skin, eyes, eyelashes or lips) by applying compositions of the present invention to the keratinous material in an amount sufficient to treat, care for and/or make up the keratinous material.

The present invention also relates to methods of enhancing the appearance of keratinous material (for example, skin, eyes, eyelashes, or lips) by applying compositions of the present invention to the keratinous material in an amount sufficient to enhance the appearance of the keratinous material.

The present invention further relates to compositions having improved cosmetic properties such as, for example, increased anti-smudging properties, increased long wear properties, and/or better texture or feel upon application.

The present invention also relates to methods of improving the feel or texture properties of a composition upon application to a keratin material comprising adding to a composition (for example, a foundation) at least one acrylic thickener and at least one oil.

It is to be understood that both the foregoing general description and the following detailed description are exemplary and explanatory only, and are not restrictive of the invention.

DETAILED DESCRIPTION OF THE INVENTION

Figure 1A:
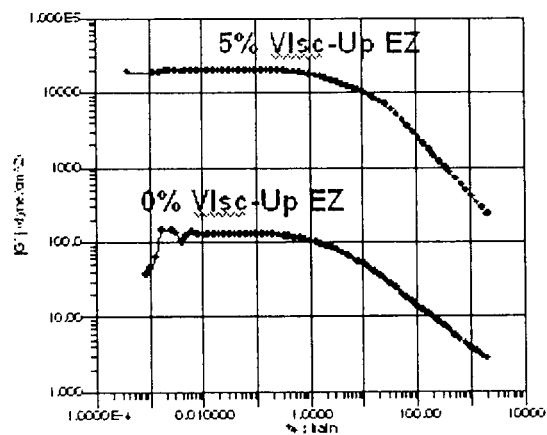
FIG. 1 is a graphic demonstration of the results from example 1 in which the rheological properties of mascara was determined, one of which contained 5% Viscup EZ and one of which contained no Viscup EZ, in oscillation mode (FIG. 1(a)) and flow mode (FIG. 1(b)).

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to lips followed by rubbing a material, for example, a sheet of paper, against the lips after expiration of a certain amount of time following application, such as 2 minutes after application. Similarly, transfer resistance of a composition may be evaluated by the amount of product transferred from a wearer to any other substrate, such as transfer from the lips of an individual to a collar when putting on clothing after the expiration of a certain amount of time following application of the composition to the lips. The amount of composition transferred to the substrate (e.g., collar, or paper) may then be evaluated and compared. For example, a composition may be transfer resistant if a majority of the product is left on the wearer's lips. Further, the amount transferred may be compared with that transferred by other compositions, such as commercially available compositions. In a preferred embodiment of the present invention, little or no composition is transferred to the substrate from the lips.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to lips and evaluating the color of the composition after an extended period of time. For example, the color of a composition may be evaluated immediately following application to lips and these characteristics may then be re-evaluated and compared after a certain amount of time. Further, these characteristics may be evaluated with respect to other compositions, such as commercially available compositions.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100° C.

"Non-volatile", as used herein, means having a flash point of greater than about 100° C.

The composition of the present invention may be in any form, either liquid or non-liquid (semi-solid, soft solid, solid, etc.). For example, it may be a paste, a solid, a gel, or a cream. It may be an emulsion, such as an oil-in-water or water-in-oil emulsion, a multiple emulsion, such as an oil-in-water-in-oil emulsion or a water-in-oil-in-water emulsion, or a solid, rigid or supple gel. The composition of the invention may, for example, comprise an external or continuous fatty phase. The composition can also be a molded composition or cast as a stick or a dish.

Depending on the intended application, such as a stick, hardness of the composition may also be considered. The hardness of a composition may, for example, be expressed in gramforce (gf). The composition of the present invention may, for example, have a hardness ranging from 20 gf to 2000 gf, such as from 20 gf to 900 gf, and further such as from 20 gf to 600 gf.

This hardness is measured in one of two ways. A first test for hardness is according to a method of penetrating a probe into the composition and in particular using a texture analyzer (for example TA-XT2i from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 gf.

The second test for hardness is the "cheese wire" method, which involves cutting an 8.1 mm or preferably 12.7 mm in diameter stick composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 gf to 300 gf, such as from 30 gf to 250 gf, for a sample of 8.1 mm in diameter stick, and further such as from 30 gf to 200 gf, and also further such as from 30 gf to 120 gf for a sample of 12.7 mm in diameter stick.

The hardness of the composition of the present invention may be such that the compositions are self-supporting and can easily disintegrate to form a satisfactory deposit on keratin materials. In addition, this hardness may impart good impact strength to the inventive compositions, which may be molded or cast, for example, in stick or dish form.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within preferred embodiments of the invention.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 25° C., 37° C., 45° C. and under freeze-thaw conditions. A composition is considered to lack stability if in any of these tests an abnormality that impedes functioning of the composition is observed. The skilled artisan will readily recognize an abnormality that impedes functioning of a composition based on the intended application.

The cosmetic compositions and methods of the present invention can comprise, consist of, or consist essentially of the essential elements and limitations of the invention described herein, as well as any additional or optional ingredients, components, or limitations described herein or otherwise useful in personal care.

Acrylic Thickener

According to the present invention, compositions comprising at least one acrylic thickener are provided. "Acrylic thickener" as used herein refers to polymers based upon one or more (meth)acrylic acid (and corresponding (meth)acrylate) monomers or similar monomers.

According to preferred embodiments, the acrylic thickener is an anionic acrylic polymer comprising at least one monomer performing a weak acid function such as, for example, acrylic acid, methacrylic acid, itaconic acid, crotonic acid, maleic acid and/or fumaric acid.

According to preferred embodiments, the acrylic thickener is an anionic acrylic polymer further comprising at least one monomer performing a strong acid function such as, for example, monomers having a function of the sulfonic acid type or phosphonic acid type, such as 2-acrylamido-2-methylpropane sulfonic acid (AMPS).

According to preferred embodiments, the anionic acrylic polymer may be crosslinked (or branched). Suitable examples of acceptable crosslinking agents include, but are not limited to, methylene bisacrylamide (MBA), ethylene glycol diacrylate, polyethylene glycol dimethacrylate, diacrylamide, cyanomethacrylate, vinyloxyethacrylate or meth-acrylate, formaldehyde, glyoxal, and compositions of the glycidylether type such as ethyleneglycol diglycidylether, or epoxydes.

Particularly preferred acrylic thickeners are disclosed in U.S. patent application publication nos. 2004/0028637 and 2008/0196174, the entire contents of both of which are incorporated herein by reference. Particularly preferred acrylic thickeners are sodium acrylate/sodium acryloyldimethyl taurate. A particularly preferred acrylic thickener is that sold under the INCI name Sodium Acrylate/Sodium Acryloyldimethyl Taurate Copolymer & Hydrogenated Polydecene & Sorbitan Laurate & Trideceth-6 which is marketed by Arch Personal Care Products, South Plainfield, N.J., USA under the tradename ViscUp®EZ.

Preferably, the acrylic thickener(s) represent from about 0.1% to about 20% of the total weight of the composition, more preferably from about 1% to about 10% of the total weight of the composition, and most preferably from about 2.5% to about 7.5%, including all ranges and subranges therebetween.

The acrylic thickeners of the present invention allow for viscous compositions containing a low solid content to be produced. For example, compositions having a viscosity above $1 \times 10^4$ poise, preferably above $5 \times 10^4$ poise, and preferably above $1 \times 10^5$ poise, can be prepared despite having a solid content lower than 30%, preferably lower than 25%, and preferably lower than 18%, owing to the presence of the acrylic thickener. Here, "solid content" refers to materials which are solid at room temperature (for example, pigments, fillers, and waxes).

Water

According to preferred embodiments of the present invention, the compositions of the present invention further comprise water. In such embodiments, water is preferably present in an amount ranging from about 30 to about 95%, preferably from about 50 to about 92%, and more preferably from about 70 to about 90% relative to the total weight of the composition, including all ranges and subranges therebetween. Preferably, such water-containing cosmetic compositions are lip compositions (for example, lipstick or liquid lip colors), and are emulsions or dispersions.

According to particularly preferred embodiments, the compositions of the present invention are in the form of an emulsion. Suitable emulsion forms include but are not limited to oil-in-water, water-in-oil, oil-in-water-in-oil, water-in-oil-in-water and nanoemulsions (emulsions whose oil globules are of very fine particle size, that is to say that they have a number-average size of less than about 100 nanometers (nm)). Emulsions contain at least one oil phase and at least one aqueous phase. Typically speaking, emulsions contain surfactants or surfactant-like materials which provide stability to the emulsions and inhibit de-phasing of the emulsions.

Oil Phase

According to the present invention, compositions comprising at least one fatty substance are provided. Suitable fatty substances include oil(s) and/or wax(es). "Oil" means any non-aqueous medium which is liquid at ambient temperature (25° C.) and atmospheric pressure (760 mm Hg). A "wax" for the purposes of the present disclosure is a lipophilic fatty compound that is solid at ambient temperature (25° C.) and changes from the solid to the liquid state reversibly, having a melting temperature of more than 30° C. and, for example, more than 45° C., which can be as high as 150° C., a hardness of more than 0.5 MPa at ambient temperature, and an anisotropic crystalline organization in the solid state. By taking the wax to its melting temperature, it is possible to use wax(es) by themselves as carriers and/or it is possible to make wax(es) miscible with the oils to form a microscopically homogeneous mixture.

Suitable oils include volatile and/or non-volatile oils. Such oils can be any acceptable oil including but not limited to silicone oils and/or hydrocarbon oils.

According to certain embodiments, the composition of the present invention preferably comprise one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, a volatile linear silicone oil may be employed in the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to other embodiments, the composition of the present invention preferably comprises one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_8$ to $C_{18}$ alkanes such as $C_8$ to $C_{18}$ isoalkanes (also known as isoparaffins), isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
|---|---|
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatility of the solvents/oils can be determined using the evaporation speed as set forth in U.S. Pat. No. 6,338,839, the contents of which are incorporated by reference herein.

According to other embodiments of the present invention, the composition comprises at least one non-volatile oil. Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms;

$C_8$ to $C_{26}$ fatty alcohols, for instance oleyl alcohol, cetyl alcohol, stearyl alcohol, and cetearly alcohol; and mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

According to preferred embodiments of the present invention, the oil is a high viscosity oil which is a silicone oil and/or a hydrocarbon oil. "High viscosity" means an oil having a viscosity greater than 250 cSt at 25° C.

Suitable examples of such silicone oils include, but are not limited to, non-volatile silicone fluids such as, for example, polyalkyl (aryl) siloxanes. Suitable polyalkyl siloxanes include, but are not limited to, polydimethyl siloxanes, which have the CTFA designation dimethicone, polydiethyl siloxane, phenyl trimethicone, trimethyl pentaphenyl trisiloxane, phenyldimethicone, phenyltrimethylsiloxydiphenylsiloxane, diphenyldimethicone, and diphenylmethyldiphenyltrisiloxane and those siloxanes disclosed in U.S. patent application publication no. 2004/0126350, the entire disclosure of which is hereby incorporated by reference. Specific examples of suitable high viscosity silicone oils include, but are not limited to, 15 M 30 from PCR (500 cSt) or Belsil PDM 1000 (1 000 cSt) from Wacker and Dow Corning 200 (350 cSt) (the values in parenthesis represent viscosities at 25° C.).

Suitable examples of such hydrocarbon oils include, but are not limited to, fluids having a molecular mass of more than 500 g/mol, for example more than 600 g/mol, and for example more than 650 g/mol. By "hydrocarbon" compound, it is meant a compound comprising principally atoms of carbon and hydrogen and optionally one or more functional groups chosen from hydroxyl, ester, ether and carboxyl functions. These compounds are, according to one aspect, devoid of —Si—O— groups. Suitable examples of hydrocarbon fluids include, but are not limited to polybutylenes, such as Indopol H-100 (of molar mass or MM=965 g/mol), Indopol H-300 (MM=1 340 g/mol), and Indopol H-1500 (MM=2 160 g/mol), which are sold or manufactured by Amoco; hydrogenated polyisobutylenes, such as Panalane H-300 E, sold or manufactured by Amoco (M=1 340 g/mol), Viseal 20000 sold or manufactured by Synteal (MM=6 000 g/mol), and Rewopal PIB 1000, sold or manufactured by Witco (MM=1 000 g/mol); polydecenes and hydrogenated polydecenes, such as Puresyn 10 (MM=723 g/mol) and Puresyn 150 (MM=9 200 g/mol) sold or manufactured by Mobil Chemicals; esters such as linear fatty acid esters having a total carbon number ranging from 30 to 70, such as pentaerythrityl tetrapelargonate (MM=697.05 g/mol); hydroxy esters, such as diisostearyl malate (MM=639 g/mol); aromatic esters such as tridecyl trimellitate (MM=757.19 g/mol); esters of C24-C28 branched fatty acids or fatty alcohols, such as those described in EP-A-0 955 039, for example triisocetyl citrate (MM=856 g/mol), pentaerythrityl tetraisononanoate (MM=697.05 g/mol), glyceryl triisostearate (MM=891.51 g/mol), glyceryl 2-tridecyltetradecanoate (MM=1 143.98 g/mol), pentaerythrityl tetraisostearate (MM=1 202.02 g/mol), poly-2-glyceryl tetraisostearate (MM=1 232.04 g/mol) and pentaerythrityl 2-tetradecyltetradecanoate (MM=1 538.66 g/mol); and mixtures thereof. Suitable ester oils can also be described according to formula $R_1COOR_2$ in which $R_1$ represents a linear or branched higher fatty acid residue containing from 1 to 40 carbon atoms, including from 7 to 19 carbon atoms, and $R_2$ represents a branched hydrocarbon-based chain containing from 1 to 40 carbon atoms, including from 3 to 20 carbon atoms, with $R_1+R_2 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters. A particularly preferred ester is diisostearyl malate.

According to preferred embodiments, the at least one oil is present in the compositions of the present invention in an amount ranging from about 0.1 to about 30% by weight, more preferably from about 0.5% to about 15% by weight, and most preferably from about 1% to about 5% by weight, based on the total weight of the composition, including all ranges and subranges within these ranges.

According to preferred embodiments of the present invention, the compositions of the present invention comprise at least one wax. Suitable examples of waxes that can be used in accordance with the present disclosure include those generally used in the cosmetics field: they include those of natural origin, such as beeswax, carnauba wax, candelilla wax, ouricoury wax, Japan wax, cork fibre wax or sugar cane wax, rice wax, montan wax, paraffin wax, lignite wax or microcrystalline wax, ceresin or ozokerite, and hydrogenated oils such as hydrogenated castor oil or jojoba oil; synthetic waxes such as the polyethylene waxes obtained from the polymerization or copolymerization of ethylene, and Fischer-Tropsch waxes, or else esters of fatty acids, such as octacosanyl stearate, glycerides which are concrete at 30° C., for example at 45° C., silicone waxes, such as alkyl- or alkoxydimethicones having an alkyl or alkoxy chain ranging from 10 to 45 carbon atoms, poly(di)methylsiloxane esters which are solid at 30° C. and whose ester chain comprising at least 10 carbon atoms, or else di(1,1,1-trimethylolpropane) tetrastearate, which is sold or manufactured by Heterene under the name HEST 2T-4S, and mixtures thereof.

If present, the wax or waxes may be present in an amount ranging from 0.1 to 50% by weight relative to the total weight of the composition, for example from 1 to 30%, and for example from 3 to 25%, including all ranges and subranges therebetween. Preferably, however, the compositions of the present invention contain a low amount of wax: that is, less than 10% wax, preferably less than 5% wax, and preferably less than 2% wax.

According to preferred embodiments, the acrylic thickener and the fatty substance(s) are present in the compositions of the present invention in a weight ratio of 1:2 to 1:20, preferably 1:3 to 1:15, and preferably 1:4 to 1:12, including all ranges and subranges therebetween.

Surfactants

According to preferred embodiments, the compositions of the present invention further comprise at least one surfactant. Suitable surfactants for use in accordance with the present invention are not limited, and include any surfactant typically used in cosmetic compositions.

Examples of acceptable surfactants for use in the compositions of the present invention include, but are not limited to, nonionic surfactants such as linear or branched polyglycerol alkyl ethers, such as, for example, Polyglyceryl-2 oleyl ether or Polyglyceryl-4 oleyl ether; Ethoxylated alkylphenols having an alkyl chain comprising from 8 to 26 carbon atoms, for example ethoxylated alkylphenols having an alkyl chain comprising 9 carbon atoms (CTFA name: Nonoxynol), such as Nonoxynol-2, for example the product sold under the name Igepal CO-210 by Rhone-Poulenc, and their mixtures; Esters of polyols derived from fatty acids comprising from 8 to 30 carbon atoms, and their oxyalkylenated and in particular oxyethylenated derivatives, the polyols preferably being chosen from sugars, C2-C6 alkylene glycols, glycerol, polyglycerols, sorbitol, sorbitan, polyethylene glycols, polypropylene glycols and their mixtures.

Further specific examples include, glycerol esters, of monoglycerides, such as monoolein (glyceryl oleate); monolinolein (glyceryl linoleate); monolaurin (glyceryl laurate), and their mixtures; polyglycerol esters, of diglyceryl monoisostearate, diglyceryl oleate, triglyceryl monooleate, diglyceryl distearate, pentaglyceryl tristearate and their mixtures; oxyethylenated glycerol ester, of, for example, oxyethylenated glycerol stearate comprising 20 oxyethylene units, such as the product sold under the name Tagat S by Goldschmidt; sorbitan esters, of, for example, sorbitan stearate, such as the product sold under the name Span 60 by ICI, sorbitan laurate, such as the product sold under the name Span 20 by ICI, sorbitan palmitate, such as the product sold under the name Span 40 by ICI, sorbitan tristearate, such as the product sold under the name Span 65 by ICI, sorbitan oleate, such as the product sold under the name Span 80 by ICI, and sorbitan trioleate, such as the product sold under the name Span 85 by ICI. Mention may be made, as oxyethylenated sorbitan ester, of the Polysorbates and, for example, Polysorbate 21, sold under the name Tween 40 by ICI, and their mixtures; sugar esters, of those derived from the following sugars: sucrose, glucose, fructose, mannose, galactose, arabinose, xylose, maltose, cellobiose, lactose, trehalose, raffinose or gentianose (for example, of sucrose cocoate, sucrose monooctanoate, sucrose monodecanoate, sucrose monolaurate, sucrose monomyristate, sucrose monopalmitate, sucrose monostearate, sucrose monooleate, sucrose monolinoleate, sucrose dioleate, sucrose dipalmitate, sucrose distearate, sucrose dilaurate, sucrose dilinoleate, sucrose tristearate, esters of octyl-.beta.-glucofuranoside, the Galactolipids sold by Scotia Lipid Teknik, and their mixtures); and Polyol ethers derived from alcohols comprising from 8 to 30 carbon atoms and in particular sugar ethers, such as glucose ethers, for example, in particular, alkylpolyglucosides (APG), such as decylglucoside ((C9/C11 alkyl)polyglucoside (1,4)) such as the product sold under the name Mydol 10 by Kao Chemicals or under the name Plantaren 2000 UP by Henkel.

Suitable surfactants also include "alkoxylated fatty alcohols"—any fatty alcohol which comprises a carbon chain having at least 5 carbon atoms (excluding the alkoxy group) and at least one alkoxy group. For example, the at least one alkoxylated fatty alcohol may have a carbon chain of C8 or greater, C10 or greater, or C12 or greater. In one embodiment, the at least one alkoxylated fatty alcohol is chosen from ethoxylated fatty alcohols. In one embodiment, the at least one alkoxylated fatty alcohol is chosen from alkoxy esters of polyglyceryl.

Non-limiting examples of suitable alkoxylated fatty alcohols include ceteareth compounds (ceteareth-2, ceteareth-3, ceteareth-4, etc.), deceth compounds (deceth-3, deceth-5, deceth-6, etc.), laureth compounds (laureth-1, laureth-2, laureth-3, etc.), oleth compounds (for example, oleth-5), steareth compounds (for example, steareth-2, steareth-10), polyglyceryl 4-lauryl ether, polyglyceryl 4-oleyl ether, polyglyceryl 2-oleyl ether, polyglyceryl 2-cetyl ether, polyglyceryl 6-cetyl ether, polyglyceryl 6-oleylcetyl ether, polyglyceryl 6-octadecyl ether, C9-11 pareth-3, C9-11 pareth-6, C11-15 pareth-3, C11-15 pareth-5, and C11-15 pareth-12.

If present, the at least surfactant is present in the compositions of the present invention in an amount ranging from about 3% to about 30% by weight, more preferably from about 5% to about 20% by weight, and most preferably from about 8% to about 12% by weight, based on the total weight of the composition, including all ranges and subranges within these ranges.

Coloring Agents

According to preferred embodiments of the present invention, compositions further comprising at least one coloring agent are provided. Preferably, such colored compositions can be cosmetic compositions such as, for example, lip compositions (for example, lipstick or liquid lip colors), mascaras, nail polish or foundations.

According to this embodiment, the at least one coloring agent is preferably chosen from pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%, including all ranges and subranges therebetween.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.1% to 20%, preferably from 0.1% to 15%, including all ranges and subranges therebetween.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the pigments may be present in the composition in a concentration ranging up to 50% by weight of the total weight of the composition, such as from 0.5% to 40%, and further such as from 2% to 30%, including all ranges and subranges therebetween. In the case of certain products, the pigments, including nacreous pigments, may, for example, represent up to 50% by weight of the composition.

Additional Additives

The composition of the invention can also comprise any additive usually used in the field under consideration. For example, dispersants such as poly(12-hydroxystearic acid), antioxidants, film forming agents, essential oils, sunscreens, preserving agents, fragrances, fillers, neutralizing agents, cosmetic and dermatological active agents such as, for example, emollients, moisturizers, vitamins, essential fatty acids, surfactants, silicone elastomers, pasty compounds, viscosity increasing agents such as waxes or liposoluble/lipodispersible polymers, and mixtures thereof can be added. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* ($9^{th}$ ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable medium and should be able to be applied to the eyelashes of human beings.

According to preferred embodiments of the present invention, methods of treating, caring for and/or making up keratinous material such as skin, lips, eyes and eyelashes by applying compositions of the present invention to the keratinous material in an amount sufficient to treat, care for and/or make up the keratinous material are provided. Preferably, "making up" the keratin material includes applying at least one coloring agent to the keratin material in an amount sufficient to provide color to the keratin material.

According to yet other preferred embodiments, methods of enhancing the appearance of keratinous material by applying compositions of the present invention to the keratinous material in an amount sufficient to enhance the appearance of the keratinous material are provided.

In accordance with the preceding preferred embodiments, the compositions of the present invention comprising at least one acrylic thickener and at least one high viscosity hydrocarbon oil are applied topically to the desired area of the keratin material in an amount sufficient to treat, care for and/or make up the keratinous material, to cover or hide defects associated with keratinous material, skin imperfections or discolorations, or to enhance the appearance of keratinous material. The compositions may be applied to the desired area as needed, preferably once or twice daily, more preferably once daily and then preferably allowed to dry before subjecting to contact such as with clothing or other objects (for example, a glass or a topcoat). Preferably, the composition is allowed to dry for about 1 minute or less, more preferably for about 45 seconds or less. The composition is preferably applied to the desired area that is dry or has been dried prior to application, or to which a basecoat has been previously applied.

According to a preferred embodiment of the present invention, compositions having improved cosmetic properties such as, for example, improved feel upon application (for example, texture, reduced drag, spreadability, bounciness, creaminess and/or reduced tackiness), increased anti-smudging properties, increased pick up by the consumer during application (that is, amount of product "picked up" out of the container) and/or increased long wear properties are provided.

According to other embodiments of the present invention, methods of improving the anti-smudging, transfer-resistance, adherence and/or long wear properties of a composition, comprising adding at least one acrylic thickener and at least one high viscosity hydrocarbon oil to the composition are provided.

According to further embodiments of the present invention, methods of improving the feel or texture of a composition, preferably a makeup compositions such as a foundation or lip composition, comprising adding at least one acrylic thickener and at least one high viscosity hydrocarbon oil to the composition are provided Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

|   |   | Comparative | Inventive |
|---|---|---|---|
| A | Steareth-2 | 2.30% | 2.30% |
| A | Steareth-20 | 4.80% | 4.80% |
| A | Cetyl Alcohol | 2.1% | 2.1% |
| A | Ethylparaben | 0.14% | 0.14% |
| A | SODIUM ACRYLATE/SODIUM ACRYLOYLDIMETHYL TAURATE COPOLYMER (and) SORBITAN LAURATE (and) TRIDECETH-6 | 0% | 5.00% |
| B | DI Water | 63.39% | 58.39% |
| B | Disodium EDTA | 0.07% | 0.07% |
| B | Potassium Cetyl Phosphate | 1.70% | 1.70% |
| B | Methylparaben | 0.15% | 0.15% |
| B | Pentylene Glycol | 2.00% | 2.00% |
| C | carbon black dispersion | 8.00% | 8.00% |
| D | Polyurethane Dispersion | 15.00% | 15.00% |
| E | PHENOXYETHANOL | 0.35% | 0.35% |
| Total |   | 100% | 100 |

Procedure

In metal container A, All phase A materials were added and heated until 90° C. (solids melted and became uniform)

In side beaker B, all phase B materials were mixed, and heated until 85° C.

When both metal container A and side tank B were at the same temperature 85° C. Added Beaker A into beaker B and homogenized for 30 minutes at 700 RPM.

After the mixture was uniform, added C carbon black dispersion and the mixture was mixed mechanically with a stirring rod until uniform.

Then, the mixture began to be cooled naturally. Added D Polyurethane Dispersion at 55° C. into the mixture Added E PHENOXYETHANOL at 40° C.

Experimental Data

Viscup EZ Effect on Rheology.

The rheological properties of the mascara composition, in accordance with the present invention, can be determined by using a controlled stress rheometer, commercially available from TA Instruments under the name AR-G2. The samples are measured using a parallel plate having a stainless steel, cross hatched, 40 mm diameter plate. The gap is set at 1,000 microns.

Figure 1B:
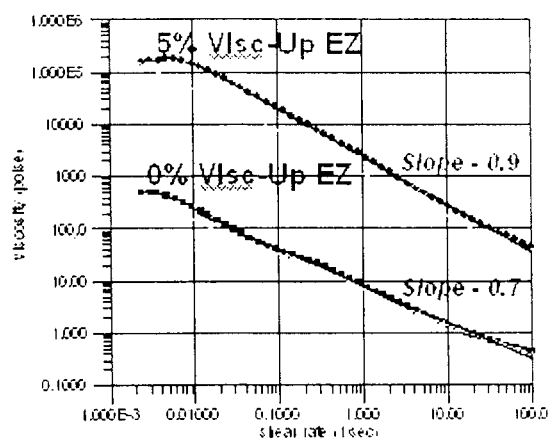

A mascara sample containing 5% Viscup EZ and one containing no Viscup EZ (control) were transferred to the rheometer, and held at 25° C. Both oscillation mode (FIG. 1(a)) and flow mode (FIG. 1(b)) were utilized to characterize the samples. It shows that comparing to control, the inventive formula had a higher Modulus and a higher viscosity (both around a factor of 2 higher than the control), indicating a higher volume and stability. The inventive formula also had a steeper shear thinning slope (−0.9) compared to the control (slope=−0.7), indicating a smoother application.

What is claimed is:

1. A composition comprising sodium acrylate/sodium acryloyldimethyl taurate copolymer, sorbitan laurate, Trideceth-6 thickener and at least one fatty substance, wherein the composition has a viscosity of at least $1\times10^4$ Poise and a solids content of 30% or lower and the composition does not comprise a silicone elastomer, wherein the at least one fatty substance is an oil having a viscosity of at least 350 cSt at 25° C. and wherein the oil is present in an amount of 1.0% to 30% by weight of the weight of the composition.

2. The composition of claim 1, wherein the composition has a solids content of 18% or lower.

3. The composition of claim 1, wherein the composition has a viscosity of at least $1\times10^5$ Poise.

4. The composition of claim 3, wherein the composition has a solids content of 18% or lower.

5. The composition of claim 1, in the form of a mascara.

6. The composition of claim 1, in the form of an emulsion.

7. The composition of claim 1, further comprising water.

8. The composition of claim 7, wherein water is present in an amount of 30% to 95% by weight of the weight of the composition.

9. The composition of claim 1, further comprising at least one coloring agent.

10. The composition of claim 1, further comprising at least one surfactant.

11. The composition of claim 1, wherein the thickener is present in an amount of 0.1% to 20% by weight of the weight of the composition.

12. The composition of claim 1, wherein the thickener and the fatty substance(s) are present in a weight ratio of 1:2 to 1:20.

13. A method of making up skin comprising applying a composition to the skin, wherein the composition comprises sodium acrylate/sodium acryloyldimethyl taurate copolymer thickener, and at least one fatty substance, wherein the composition has a viscosity of at least $1\times10^4$ Poise and a solids content of 30% or lower and the composition does not comprise a silicone elastomer.

14. A method of making up lips comprising applying a composition to the lips, wherein the composition comprises sodium acrylate/sodium acryloyldimethyl taurate copolymer thickener, and at least one fatty substance, wherein the composition has a viscosity of at least $1\times10^4$ Poise and a solids content of 30% or lower and the composition does not comprise a silicone elastomer.

15. A method of making up eyelashes comprising applying composition to the eyelashes, wherein the composition comprises sodium acrylate/sodium acryloyldimethyl taurate copolymer, sorbitan laurate, Trideceth-6 thickener, and at least one fatty substance, wherein the composition has a viscosity of at least $1\times10^4$ Poise and a solids content of 30% or lower and the composition does not comprise a silicone elastomer.

16. The method of claim 13, wherein the composition has a solids content of 18% or lower.

17. The method of claim 13, wherein the composition has a viscosity of at least $1\times10^5$ Poise.

18. The method of claim 13, wherein the composition is in the form of an emulsion.

19. The method of claim 13, wherein the composition further comprises water.

20. The method of claim 13, wherein water is present in an amount of 30% to 95% by weight of the weight of the composition.

21. The method of claim 13, wherein the composition further comprises at least one coloring agent.

22. The method of claim 13, wherein the composition further comprises at least one surfactant.

23. The method of claim 13, wherein the thickener is present in an amount of 0.1% to 20% by weight of the weight of the composition.

24. The method of claim 13, wherein the thickener and the fatty substance(s) are present in a weight ratio of 1:2 to 1:20.

25. The method of claim 14, wherein the composition has a solids content of 18% or lower.

26. The method of claim 14, wherein the composition has a viscosity of at least $1\times10^5$ Poise.

27. The method of claim 14, wherein the composition is in the form of an emulsion.

28. The method of claim 14, wherein the composition further comprises water.

29. The method of claim 28, wherein water is present in an amount of 30% to 95% by weight of the weight of the composition.

30. The method of claim 14, wherein the composition further comprises at least one coloring agent.

31. The method of claim 14, wherein the composition further comprises at least one surfactant.

32. The method of claim 14, wherein the thickener is present in an amount of 0.1% to 20% by weight of the weight of the composition.

33. The method of claim 14, wherein the thickener and the fatty substance(s) are present in a weight ratio of 1:2 to 1:20.

\* \* \* \* \*